United States Patent
Kandel et al.

[11] Patent Number: 6,077,989
[45] Date of Patent: Jun. 20, 2000

[54] RESORBABLE IMPLANT BIOMATERIAL MADE OF CONDENSED CALCIUM PHOSPHATE PARTICLES

[76] Inventors: Rita Kandel, 430 Heath Street East, Toronto Ont, Canada, M4G 1B5; Robert Pilliar, 56 Rochester Avenue, Toronto Ont, Canada, M4N 1N8; Marc Grynpas, 55 Duncannon Drive, Toronto Ont, Canada, M5P 2M2

[21] Appl. No.: 09/194,159
[22] PCT Filed: May 15, 1997
[86] PCT No.: PCT/CA97/00331
§ 371 Date: Nov. 23, 1998
§ 102(e) Date: Nov. 23, 1998
[87] PCT Pub. No.: WO97/45147
PCT Pub. Date: Dec. 4, 1997

Related U.S. Application Data
[60] Provisional application No. 60/018,525, May 28, 1996.

[51] Int. Cl.$^7$ ........................................... A61F 2/02
[52] U.S. Cl. ............................................... 623/16
[58] Field of Search ................. 623/11, 16, 17, 623/19, 18, 22, 23, 901

[56] References Cited

U.S. PATENT DOCUMENTS

| | | | |
|---|---|---|---|
| 4,000,525 | 1/1977 | Klawitter et al. | 3/1.911 |
| 4,330,891 | 5/1982 | Branemark et al. | 3/1 |
| 4,360,625 | 11/1982 | Griffith . | |
| 4,553,373 | 11/1985 | Mears . | |
| 4,655,777 | 4/1987 | Dunn et al. | 623/16 |
| 5,077,079 | 12/1991 | Kawamura . | |
| 5,108,755 | 4/1992 | Daniels . | |
| 5,326,357 | 7/1994 | Kandel . | |
| 5,338,772 | 8/1994 | Bauer et al. . | |
| 5,639,402 | 6/1997 | Barlow et al. | 264/6 |
| 5,677,355 | 10/1997 | Shalaby et al. | 521/61 |
| 5,969,020 | 10/1999 | Shalaby et al. | 524/167 |

FOREIGN PATENT DOCUMENTS 2 374 020  7/1978  France .

OTHER PUBLICATIONS

Phosphate Fibres, Edward J. Griffith, Plenum Press, 1995 pp. 91, 92, 190 and 214.

Abstract for Third Canadian Connective Tissue Conference, Queen's University, Kingston, Ontario, Canada, May, 1997.

Abstract—In Vitro Formation of Minerlized Cartilagenous Tissue by Articular Chondrocytes, R. A. Kandel et al, Society for In Vitro Biology, In Vitro Cell. Div. Biol.—Animal 33:174–181, Mar. 1997.

Evaluation of New High–Performance Calcium Polyphosphate Bioceramics as Bone Graft Materials, S. R. Nelson et al, J Oral Maxillofac Surg 51:1363–1371, 1993.

Mechanical Properties of Biodegradable Polymers and Composites Proposed for Internal Fixation of Bone, A. U. Daniels et al; Journal of Applied Biomaterials, vol. 1, 57–78 (1990).

Calcium Polyphosphate Fibres for Composite Biomaterials—Degradation Studies; Wensu Guo et al; Centre for Biomaterials, University of Toronto, 20$^{th}$ Annual Meeting of the Society for Biomaterials, Apr. 1994, p. 163.

*Primary Examiner*—Todd E. Manahan
*Assistant Examiner*—Eduardo C. Robert
*Attorney, Agent, or Firm*—Riches, McKenzie & Herbert

[57] ABSTRACT

A resorbable biomaterial for implantation in humans and other animals comprises amorphous or crystalline condensed calcium phosphate of the general formula: $[Ca(PO_3)_2]_n$, where n is 3 or greater and the molar ratio of Ca:P is between about 0.4 and 0.6. The condensed calcium phosphate powder can be formed as a sintered powder which is bound or consolidated to form at least part of an implantable anchor, with controlled size and amount of porosity. The condensed calcium phosphate part of anchor/implant preferably has a bone interfacing portion which is placed in juxtaposition with adjacent hard tissues when implanted in a patient, and which is characterized by interconnected pores extending from the exterior throughout the interior of the biomaterial. The condensed calcium phosphate may be used to replace hard connective tissues, or to regenerate soft connective tissues by providing a support on which soft tissue may be grown in vitro or in vivo, or to anchor soft connective tissue to bone.

27 Claims, 5 Drawing Sheets

RESORBABLE IMPLANT BIOMATERIAL MADE OF CONDENSED CALCIUM PHOSPHATE PARTICLES

The applicant claims the benefit of 35 U.S.C. § 119(e) of U.S. Provisional Application No. 60/018,525 filed May 28, 1996.

FIELD OF THE INVENTION

The present invention relates to implants made from a resorbable biomaterial, and more particularly to a resorbable biomaterial for use in joining or anchoring soft connective tissue to hard connective tissue, leading to the creation of a natural soft tissue/hard tissue connection, a process for producing such a biomaterial, as well as biological materials incorporating such biomaterials, and methods of using the biomaterial and biological materials.

BACKGROUND OF THE INVENTION

Skeletal disorders that result from degenerative processes, such as arthritis, trauma, bone fracture, torn ligaments or tendons and congenital defects, are very common and have a great impact on patient morbidity, and health care costs in terms of days lost from work and patient hospitalization.

Various methods and materials for regenerating tissues have been developed to repair or restructure damaged or malformed connective tissues. Heretofore, however, conventional methods and materials have proven unsatisfactory for use in connecting soft tissues, such as tendons, ligaments, intervertebral disc articular cartilage and fibrocartilage to hard tissues such as bone or dentin.

Conventional methods of repairing hard connective tissues that require replacement. ie. bone, typically involves cutting or removing part or the damaged bone and then replacing the removed portion with an implanted matrix along which bone tissues will grow.

Known matrices used in bone repair have been constructed from a variety of materials including ceramics, metals such as titanium alloys, stainless steel, as well as various biodegradable polymers and composites. One known matrix disclosed in U.S. Pat. No. 5,108,755 to Daniels et al is formed from a degradable composite made up of a biodegradable polymer which is reinforced with loose or woven calcium sodium metaphosphate fibers as reinforcements. The biodegradable matrix is selected from poly(ortho ester), poly(lactic acid) and poly(glycolic acid) materials with the reinforcements made from fibers described in U.S. Pat. No. 4,346,028 which issued Aug. 24, 1982. As noted in Guo, W. et al in *Calcium Polyphosphate Fibers for Composite Biomaterials—Degradation Studies*, The 20th Annual Meeting of the Society for Biomaterials, Boston, Mass., April 1994, resorbable biomaterials having fibrous reinforcements may not be suitable for all applications. In particular, Guo suggests that calcium polyphosphate fiber reinforced composites may be susceptible to premature loss in strength and stiffness properties as a result of fiber degradation Ceramic implants made from a synthetic hydroxyapatite ($Ca_3(PO_4)_3OH$), have been proposed by Nelson et al in *Evaluation of New High-Performance Calcium Polyphosphate Bioceramics as Bone Graft Materials*, J. Oral Maxillofac Surg., 1363–1371, 1993. Hydroxyapatite has, however, proven exceptionally slow to degrade in the body and therefore not generally considered to be a suitable biodegradable material. Ceramic implants of tricalcium phosphate have also been proposed, however, these implants have been found to have rates of degradation which are too fast.

Conventional methods of repairing and reattaching soft connective tissues, such as ligaments, tendons and cartilage to bone, typically involve driving a metal pin, staple, braid or other mechanical type fastener through the soft tissues and into a patient's bone to secure a portion of the soft tissue in place. A major disadvantage of conventional methods of reattaching soft tissues to hard issues exists in that there are physical limitations as to where such conventional mechanical fasteners may be used. The use of pins, staples and the like, frequently necessitates the stretching, bending or otherwise altering the natural positioning and configuration of the soft tissue so that it is positioned at the point of reattachment. The result is therefore that soft tissues which become detached from the bone may be reattached at a location distant from the original point of natural hard tissue/soft tissue attachment. In addition, soft tissues connected by mechanical fasteners do not reattach biologically to the bone and are weakened at the site of attachment.

The possibility of reintroducing regenerated articular cartilage into a joint to replace or repair damaged cartilage is disclosed in U.S. Pat. No. 5,326,357 to Kandel, which issued Jul. 5, 1994. U.S. Pat. No. 5,326,357 describes a process by which in vitro grown cartilage is removed from a synthetic substrate prior to implantation. While reintroduced articular cartilage may permit further articular cartilage growth, Kandel fails to achieve a method or structure by which such articular cartilage may be securely reattached to a specified and preferred bone site.

SUMMARY OF THE INVENTION

To at least partially overcome the disadvantages of the prior art devices, the present invention provides a resorbable biomaterial which includes a porous end portion for mated engagement with a human or other animal's bone. The porous end portion comprises a degradable condensed calcium phosphate powder having one or more P—O—P linkages and the general formula $[Ca(PO_3)_2]_n$, such as calcium metaphosphate or calcium polyphosphate, or a biodegradable hydroxyapatite, or calcium carbonate or other biodegradable material. The powder is formed into a firm implantable structure characterized by interconnected pores having a pore size and diameter selected to permit bone tissue penetration and ingrowth therein.

Another object of the invention is to provide an implantable structure for attaching soft tissue to hard tissue and which is made from a bioresorbable material so as to be substantially replaced by such hard and soft tissues over time.

Another object of the invention is to provide an implantable anchor, connector or structure made from a resorbable biomaterial for use in repairing damaged or malformed connective tissues such as bone, and which is characterized by suitable strength and stiffness properties, so as to permit its use either in repairing bone areas subject to high stresses or as a screw, pin, staple or the like.

A further object of the invention is to provide a structure which may be used in vivo in a human to anchor soft connective tissue to hard connective tissue.

Another object of the invention is to provide a resorbable biomaterial for use in vivo in an animal which on implantation will not produce a fibrotic or cellular reaction.

Another object of the invention is to provide a resorbable implant for use in the non-mechanical attachment of soft connective tissues such as tendons, ligaments, articular cartilage, intervertebral disc, and fibrocartilage to bone at substantially natural hard tissue/soft tissue attachment sites.

A further object of the invention is to provide a resorbable biomaterial for use in vivo in a human which is made from a condensed calcium phosphate having a linear chain or linear ring structure and the general formula $[Ca(PO_3)_2]_n$, where n is 3 or greater.

The present inventors have developed a resorbable biomaterial for implantation in humans and other animals. The biomaterial comprises amorphous or more preferably crystalline condensed calcium phosphate powder of the general formula $[Ca(PO_3)_2]_n$ (ie. a calcium metaphosphate or a calcium polyphosphate) and where n is 3 or greater and the molar ratio of Ca:P is between about 0.4 and 0.6. The calcium metaphosphate may be as is disclosed in U.S. Pat. No. 4,360,625, and which issued November 1982. The inventors have appreciated a range of n values is possible for calcium metaphosphate in either amorphous or crystalline form.

The crystalline calcium polyphosphate and/or calcium metaphosphate can be formed as a sintered powder which is bound or consolidated to form at least part of an implantable anchor, with controlled size and amount of porosity. Alternately, the condensed calcium phosphate could be formed by other means such as direct solidification from a melt with pores or channels forming due to volume changes associated with liquid-to-solid state transformation, or by incorporation of sacrificial leachable/dissolvable phases, such as salt or polymer, into the structure.

The calcium polyphosphate/calcium metaphosphate part of anchor/implant preferably has a bone or dentin engaging or interfacing portion (ie. the hard tissue interfacing portion) which is placed in juxtaposition with adjacent hard tissues when implanted in a patient. The hard tissue interfacing portion is characterized by interconnected pores extending from the exterior throughout the interior of the biomaterial. The size of the pores and the volume percent porosity are selected to permit cell and hard connective tissue penetration or ingrowth, into the pores.

The anchor/implant may be used to replace hard connective tissues, but more preferably also is used to regenerate soft connective tissues by providing a support on which soft tissue may grow. Part of the implant is thus used as an attachment surface on which to place cells and grow tissue in vitro. The soft tissue attachment portion of the implant upon which soft tissues are provided may comprise condensed calcium phosphate of the general formula $[Ca(PO_3)_2]_n$, or alternately other firm biodegradable substances including calcium carbonate, hydroxyapatite, or degradable polymers such as polylactide, polyorthoesters, polyglycolide, polyhydroxybutyrate or polycaprolactone, either alone or in combination.

The in vitro grown tissues, together with anchor/implant, are then implanted into a patient with the porous inorganic material serving as a temporary anchor to hard tissue, as for example, in re-attaching torn ligaments to bone. Preferably, as soft connective tissues are harvested from a patient, cells are isolated and seeded onto the implantable form in vitro prior to its implantation into the patient, to allow formation of new tissue. The soft tissue may alternately be formed by cells isolated from other individual or animal tissue and the cultured soft tissue/calcium metaphosphate and/or calcium polyphosphate construct subsequently implanted.

In one example, a surface of an anchor is covered with chondrocytes which would form fibrocartilage, or fibroblasts, which would form tendon or ligament which on implantation is to interface with soft connective tissues (ie. the soft tissue attachment surface). In one approach, a surface portion of the implant is used for cell seeding and subsequent tissue formation in vitro, following which the biomaterial/tissue construct is implanted in a patient to allow bone ingrowth in vivo at the bone implant interface.

In another aspect, the invention relates to a process for producing a resorbable biomaterial for implantation in humans and animals comprising the steps of forming an amorphous or crystalline powder of condensed calcium phosphate of the general formula $[Ca(PO_3)_2]_n$, where n is at least 3 and the molar ratio of Ca:P is between about 0.4 to 0.6 into a shape for use as an implant or implant preform. Once the desired shape has been selected, the crystalline calcium metaphosphate/polyphosphate powder is then sintered to produce a rigid implantable structure which comprises a calcium metaphosphate portion having interconnecting pores that extend from the exterior throughout the interior of the portion, and which have a pore size and volume percent porosity which permits migration of hard tissue cells and ingrowth of hard tissues in the pores. The porous material can then be formed into the desired final shape by an appropriate machining method.

Prior to implantation, the pores of the sintered implantable structure may also be substantially infiltrated with a degradable organic strengthener phase to provide the structure with increased toughness and resiliency. The degradable organic phase is selected so as to degrade at a more rapid rate than the calcium metaphosphate/calcium polyphosphate portion of the structure. Preferred organic materials used in pore infiltration would therefore include organic polymers such as polycaprolactone, polyglycolide, polylactide and their copolymers.

The invention also relates to an implant for use in connecting soft and hard connective tissues comprising, a hard tissue interfacing portion, and a soft tissue attachment portion. The hard tissue interfacing portion comprising calcium metaphosphate and/or calcium polyphosphate particles which are joined together to form a rigid matrix characterized by interconnecting spaces between said particles that extend from an exterior substantially throughout an interior of at least part of said hard tissue interfacing portion, the interconnecting spaces having a pore size which permits bone cells and tissues to penetrate and grow therein.

The biomaterial may be provided as a preformed implantable structure containing two or more regions or zones which have different pore sizes and/or volume percent porosity. The implant may be a composite construction of two or more distinct portions each having pores with a pore size and volume percent porosity which is selected for attachment and/or ingrowth of specific cells or tissues, and having specific functional requirements vis-a-vis load carrying ability. The biomaterial may comprise a bone-interfacing or engaging zone or portion having interconnected pores with a pore size of between about 10 to 1000 $\mu$m, and more preferably 50 to 250 $\mu$m; and a soft connective tissue interfacing zone or attachment portion having interconnected pores with a pore size of between about submicron size to 250 $\mu$m, and more preferably 20 to 150 $\mu$m. The biomaterial could also contain a gradient of different pore sizes, or contain appropriate distributions of pore sizes throughout.

The invention still further relates to a biological material for implantation in humans and other animals comprising a biomaterial including substantially pure condensed calcium phosphate having the general formula $[Ca(PO_3)_2]_n$, where n is 3 or greater, and most preferably calcium metaphosphate, together with soft connective tissue, such as tendon, ligament, articular cartilage fibrocartilage or intervertebral disc attached to and physically interlocked through the pores of the biomaterial.

In another aspect, the invention resides in a method of using the biomaterial of the present invention to deliver pharmaceutical agents, growth factors incorporated within the pores of the resorbable biomaterial, and a method of using the biomaterial as a prophylactic replacement and/or in the repair of damaged or deficient tissues.

In a further aspect, the present invention resides in a method of treating deficient hard tissue and soft tissue attachment in a patient by the use of an implant comprising a hard tissue interfacing portion and a soft tissue attachment portion, said hard tissue interfacing portion which supports anchoring including condensed calcium phosphate particles joined to form a matrix characterized by interconnecting spaces which extend from an exterior throughout an interior of said matrix, said condensed calcium phosphate particles represented by the formula (1):

$$[Ca(PO_3)_2]_n \qquad (1)$$

where n is at least 3, and the molar ratio of Ca to P is between about 0.4 and 0.6, the interconnecting spaces having a pore size which permits hard connective tissue cells and tissues to penetrate therein, said method comprising the steps of:

preparing a recipient site in said patient's hard tissue, said recipient site having a complementary size and shape to said hard tissue interfacing portion of said implant, and inserting said implant in said recipient site with said hard tissue interfacing portion substantially in juxtaposition with said patient's hard tissues and said soft tissue attachment portion positioned substantially at a site of natural hard tissue/soft tissue attachment.

In another aspect, the present invention relates to a hard tissue/soft tissue construct for use in in vitro testing of pharmaceutical agents on soft tissue formation, hard tissue formation and combinations thereof.

In a further aspect, the present invention resides in a resorbable biomaterial for implantation into an animal comprising particulate condensed calcium phosphate represented by formula (1):

$$[Ca(PO_3)_2]_n \qquad (1)$$

wherein n is at least 3, and the molar ratio of Ca to P is selected between about 0.4 to 0.6.

In another aspect, the present invention resides in an implant for connecting bone tissue and soft connective tissues in a human comprising, a bone tissue interfacing portion, a soft tissue attachment and interlock portion, and soft connective tissue cells attached to said soft tissue attachment portion and with tissue formation interlocked therewith, said cells obtained from soft tissues selected from the group consisting of tendons, ligaments, cartilage and intervertebral disc, said bone tissue interfacing portion comprising a biodegradable particulate material which is bound to form a rigid matrix characterized by interconnecting pores which extend from an exterior substantially through an interior of said bone tissue interfacing portion, the pore size of said interconnecting pores selected at between about 50 to 250 μm, and said soft tissue attachment portion being characterized by pores having a pore size selected at less than 200 μm, and wherein said pores of said soft tissue attachment portion are provided in substantially non-linear communication.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which.

DETAILED DESCRIPTION OF THE INVENTION

Figure 1:
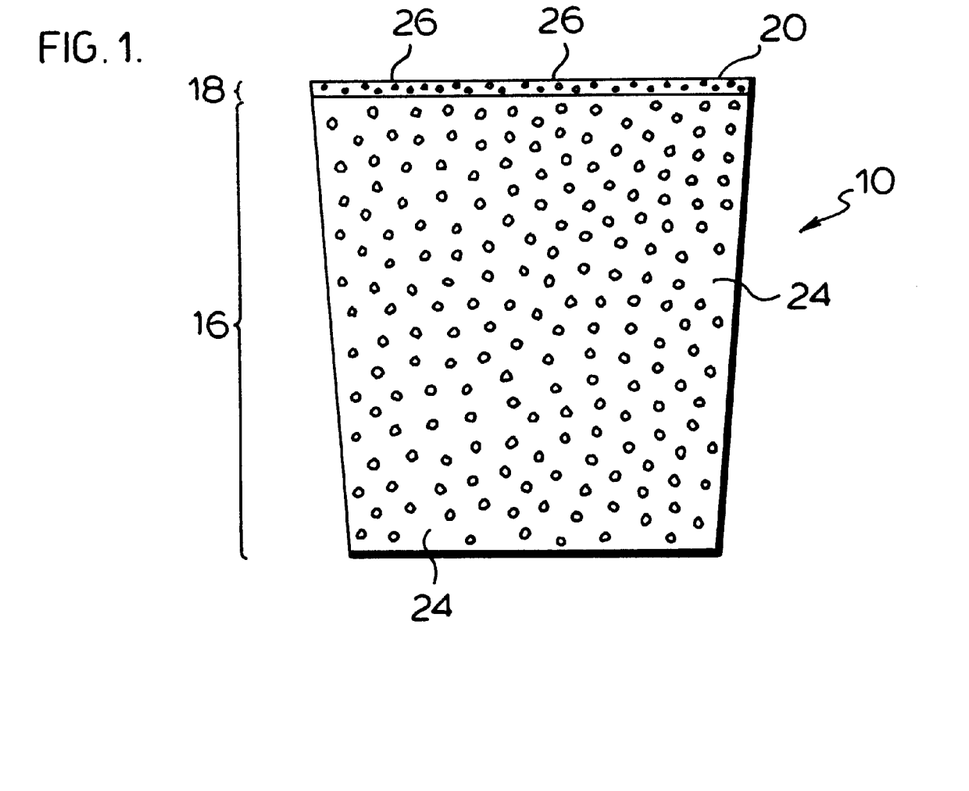
FIG. 1 shows schematically an implantable anchor device formed from a resorbable biomaterial in accordance with a first embodiment of the invention.
Figure 2:
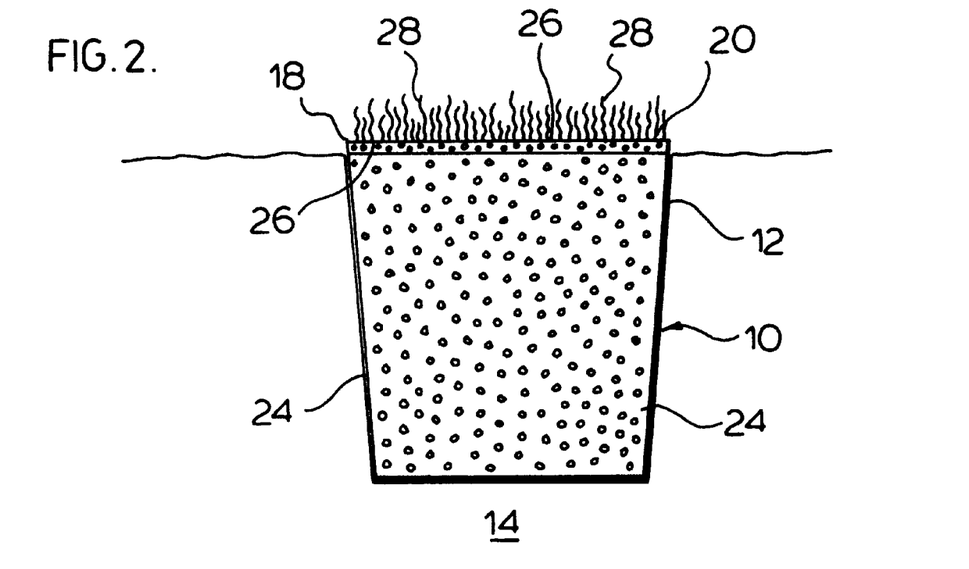
FIG. 2 shows schematically the biomaterial of FIG. 1 on initial implantation within a human bone.

As shown best in FIGS. 1 and 2, the present invention relates to an implantable anchor device 10 which is used to join soft and hard connective tissues by its implantation in humans. The anchor device 10 is formed of a resorbable biomaterial, such that following its implantation, there occurs a gradual absorption or elimination by the body of the anchor device 10 as a result of hydrolysis and/or a patient's metabolic processes. In particular, the resorbable biomaterial used to form the anchor device 10 comprises crystalline condensed calcium phosphate having one or more P—O—P linkages and represented by the general formula $[Ca(PO_3)_2]_n$ (where n is 3 or greater). Preferably, the condensed calcium phosphate is a linear calcium polyphosphate and/or a calcium metaphosphate, and most preferably a β-calcium metaphosphate, which is in particulate form, and as will be described, which is bound into a rigid implantable structure.

The anchor device 10 is formed having an overall frustoconical shape which, as is shown in FIG. 2, permits its press-fit insertion into a complementary sized cavity 12 which is formed in the region of natural soft connective tissue attachment to the patient's bone 14. The anchor 10 comprises a bone engaging or interfacing portion 16 and a soft tissue attachment region 18. The bone interfacing portion 16 corresponds generally to the portion of the implant 10 which, when initially implanted into the bone 14, is substantially in juxtaposition with the patient's bone tissues 14. The soft connective tissue attachment region 18 includes a soft tissue contact surface 20. As seen best in FIG. 2, the soft tissue attachment portion 18 is formed on part of the anchor 10 which, when implanted, locates at the site of natural soft tissue/bone attachment with the contact surface 20 in juxtaposition with detached or damaged soft tissues, to permit the attachment of tendons, ligaments and other soft connective tissues thereto. While FIG. 2 shows the region 18 as extending outwardly beyond the bone 14, it is to be appreciated that the anchor device 10 could be implanted with the soft connective tissue attachment region 18 flush with or recessed below the adjacent bone 14.

The bone interfacing portion 16 is formed from particles consisting of crystalline linear calcium polyphosphate and/or calcium metaphosphate which have been consolidated into the desired shape and sintered to form a rigid bound structure. Following sintering of the condensed calcium phosphate particles, the bone interfacing portion 16 is characterized by interconnecting pores 24 that extend from the exterior throughout part or all of the interior of the portion 16. The pores of portion 16 have a pore size which permits ingrowth of bone cells and bone tissues therein. The condensed calcium phosphate particles forming the portion 16 may be further characterized as having a calcium to phosphorous molar ratio of about 0.2 to 0.7, preferably 0.4 to 0.6, and most preferably about 0.5. The preferred tensile strength of the portion 16 as measured by diametral compressive tests is more than 5 MPa, and more preferably at least 15 MPa.

The interconnected pores 24 in the bone interfacing portion 16 permit migration of bone cells and the formation of bone within the pores as well as bone ingrowth therewith. Typically for regeneration of bone, the size of the pores 24 in the interfacing portion 16 will be between about 10 to 1000 μm in cross-sectional dimension. Where the biomaterial is used as a scaffold for cell migration and bone formation as well as bone ingrowth, the pore size is between about 20 to 1000 μm, and preferably 50 to 250 μm, in cross-sectional dimension. The volume percent porosity of the condensed calcium phosphate biomaterial of the bone interfacing portion 16 is preferably between about 5 and 65%, and most preferably about 35%.

Although not essential, the pores 24 of the portion 16 may be partially or wholly infilled with a degradable organic phase (not shown) as a strengthener. The organic phase provides enhanced toughness to the bone interfacing portion 16 of the anchor 10 on its initial placement. The organic phase may, for example, comprise polycaprolactone, polyglycolide and/or polylactide, or their copolymers, and is selected so as to biodegrade at a more rapid rate than the calcium polyphosphate/calcium metaphosphate structure. In this manner, following placement of the anchor device 10, the organic phase will preferentially degrade to permit bone cell and tissue growth between the fixed condensed calcium phosphate particles in advance of the condensed calcium phosphate degradation.

In one possible embodiment, the pores 24 of the bone interfacing portion 16 may be wholly infiltrated with an organic strengthener. Prior to implantation, the bone interfacing portion 16 may be immersed in a suitable solvent to partially dissolve the organic phase from the peripheral areas of the anchor device 10. The resulting anchor device 10 would thereby be characterized by open pores 24 about its periphery which would facilitate rapid bone tissue growth therein, and a core portion characterized by pores 24 infilled with the organic phase for increased overall strength.

The soft connective tissue attachment region 18 preferably is also formed from crystalline calcium polyphosphate and/or calcium metaphosphate particles which are bound and which are represented by the formula $[Ca(PO_3)_2]_n$, where n is at least 3, and also includes interconnecting pores 26. To permit soft connective tissue attachment and the physical interlock of soft connective tissues 28 (FIG. 2) into the pores 26 of the region 18, it is preferable that the soft tissue attachment region 18 has a porosity of between less than 1% and 35%, and more preferably about 30%. The pore size of the biomaterial used to form the region 18 preferably ranges from submicron size to about 200 μm, and preferably between 20 to 110 μm in average cross-sectional dimension.

Prior to cell seeding, implantation and degradation of the anchor 10, the pores 26 extend into the contact surface 20 on the region 18, and which is not intended for interfacing with bone 14. More preferably, substantially all interconnections between the pores 26 of the soft tissue attachment region 18 are in non-linear communication whereby in vitro flow-through of soft tissue cells therealong is limited. In this manner, soft connective tissue cells attach to the surface 20 of the region 18 and collect in any pores 26 extending therethrough. The non-linear communication of the pores in the soft tissue attachment region 18 advantageously maintains soft tissue cells seeded thereon in proximity to contact surface 20 and the region where soft tissue replacement is desired, and limits soft tissue cell movement into the bone interfacing portion 16 where they may otherwise inhibit bone ingrowth.

The anchor 10 may be formed as separate stages in which the bone interfacing portion 16 is formed independently from the soft tissue attachment region 18. Alternately, as will be described, the anchor 10 may be made as a single integral structure in which a gradient of porosities exists.

The anchor 10 may contain bioactive agents including proteins, peptides, nucleic acids, polysaccharides, lipids, and non-protein organic and inorganic compounds. The agents may have biological effects including but not limited to anti-inflammatories, antimicrobials, anti-cancer, antivirals, hormones, cytokines, antioxidants, channel blockers, and vaccines. It may also be possible to incorporate imaging agents such as barium in the biomaterial. Cell growth, differentiation, and/or migration modulators may be incorporated into the biomaterial. In addition, where the implantable anchor 10 is formed as a composite construction, the regions of the composite construction may be characterized by different pore sizes, calcium to phosphorous ratios and/or different bioactive agents.

The bioactive agent can be dispersed or embedded in the biomaterial used to form the implant 10. Implantation of the implant 10 is followed by slow hydrolysis and biological resorption of the calcium polyphosphate/calcium metaphosphate material.

The surface properties of the condensed calcium phosphate may be modified by incorporating surface agents, such as adhesion peptides into the biomaterial. By way of non-limiting example, the biomaterial may be coated with a surface agent (e.g. titanium oxide, iron oxide, polyphosphazene) which decreases the rate of degradation of the calcium metaphosphate and/or calcium polyphosphate. The implant 10 may also be provided with structural reinforcements such as degradable fibers.

In a preferred method, the anchor 10 is produced by first forming calcium metaphosphate glass or crystal powder.

Condensed calcium phosphate glass powder may be prepared by first forming condensed calcium phosphate powder from calcined calcium phosphate monobasic, $Ca(H_2PO_4)_2 \cdot H_2O$. The result of this calcining process is the formation of condensed polyphosphates by the repeated condensation and linking of tetrahedral phosphate groups. The molecular structure of the resulting calcium metaphosphate/calcium polyphosphate is a condensed calcium phosphate represented as $[Ca(PO_3)_2]_n$ with n being an integer of at least 3, preferably at least 100 and more preferably at least 400. The preferred Ca:P molar ratio is preferably about 0.5. The resulting powder may be melted and poured out onto a suitable surface to produce a solid piece of condensed calcium phosphate glass (amorphous structure) consisting of calcium polyphosphate and calcium metaphosphate. The hot glass may then be shattered (e.g. by dropping in distilled water) to produce a powder frit. Further grinding and milling then forms an amorphous condensed calcium phosphate powder of the desired size range.

The condensed calcium phosphate powder is then placed into a non-reactive mould having a size and shape suitable for forming a part for implantation in humans and animals (with or without further shaping). The condensed calcium phosphate powder is vibrated into the mould (eg. Pt or graphite moulds), with coarser powder particles filling the part of the mould used to form the bone interfacing portion 16 of the anchor 10, and finer powders used to form the soft tissue attachment region 18. The precise size of the particles is selected to allow formation of interconnecting pores with a desired pore size in the biomaterial, or for allowing infiltration by the degradable organic phase, in the case of a composite biomaterial being formed.

Optimally, to convert the amorphous powder into crystalline structures requires subjecting the mould to a modest heat treatment in an air or inert gas atmosphere. It has been determined that rapid crystallization of the calcium metaphosphate powder can occur at 600° C. or so. Depending on the particle size and the mass of powder being treated, temperatures above 600° C. (and preferably about 960° C.–970° C.) will result in fully crystallized calcium polyphosphate and/or calcium metaphosphate powders of the formula $[Ca(PO_3)_2]_n$, where n is at least 3. The annealing time being determined by the exact size and quantity of powders. It is to be appreciated that lower temperatures and longer annealing times may also be used to effect crystallization.

The condensed calcium phosphate glass or crystalline powder is sintered, as for example, by pressure or gravity sintering just below the melting temperature of the biomaterial to bind or fuse the powder particles and produce the rigid porous bound biomaterial. Sintering conditions are selected which permit the formation of interconnecting pores having the pore size and volume percent porosity. In one embodiment of the invention, the condensed calcium phosphate powder is gravity sintered for about 10 minutes to 2 or more hours, preferably at least 15 minutes, at a temperature in the range of about 830 to 970° C. and preferably about 940 to 970° C. The exact sintering temperature used is, however, dependent on the molecular weight distribution of the powders being sintered and its degree of crystallinity and Ca:P molar ratio.

The condensed calcium phosphate glass powder and/or crystal powder may be formed into an implant of any shape suitable for implantation purposes in humans and animals. For example, the condensed calcium phosphate glass or crystal powder may be formed into rods, pins, screws, and plates, either with or without infiltration of the pores of the condensed calcium phosphate structure with the organic phase. The particle size of the crystal powder used to form biomaterials is preferably in the range of 10 μm to 1000 μm in diameter. The biomaterial may also be shaped to allow different zones of the biomaterial to interface with different surfaces. For example, where one zone of the biomaterial is to interface with bone, the overall shape of the bone-interfacing zone is such that it can be press-fitted into a prepared site and remain securely fixed during the time necessary for implant stabilization by bone ingrowth.

Bioactive agents may be added to the biomaterial after the formation of the anchor 10 using conventional methods such as by surface energy driven capillary action.

It will be appreciated that other methods may be used to prepare a biomaterial of the invention. For example, laser sintering may be used to produce interconnecting pores of desired pore sizes in compacted calcium metaphosphate glass or crystal powder. The biomaterial may also be formed by direct solidification from the melt or even by the addition of a suitable binder phase. (See also Trial Example 3 for a detailed description of processes for preparing the biomaterial of the invention).

As described, the biomaterial of the invention may be used as a supporting surface for soft connective tissue formation and as a scaffold to guide the ingrowth of bone cells and anchor the soft tissues to the bone. Generally, the condensed calcium phosphate, and particularly the β-calcium metaphosphate may be used (a) in bone reconstruction, replacement, and augmentation; (b) in cosmetic surgery, in particular, to reconstruct facial bones; (c) in osteosynthesis i.e. to produce an in vivo splint; (d) to repair/replace localized regions of degenerated or damaged soft connective tissues and to reattach it to bone; as well as in dental applications. It may also be used to direct migration, differentiation, or growth of cells through the release of bioactive agents such as growth and induction factors, hormones, and cytokines.

Therefore, an anchor 10 made from bound condensed calcium phosphate particles having the formula $[Ca(PO_3)_2]_n$, where n is 3 or more and the Ca to P molar ratio is about 0.5, may be directly implanted in humans or other animals to replace damaged tissue and/or to anchor soft tissue to bone or heal a bone fracture. The condensed calcium phosphate may also be used as a support surface to allow isolated soft connective tissue cells to form soft connective tissue 28 (FIG. 2) in vitro, which becomes securely attached and physically interlocked therewith. The cells could be obtained from other sites in a patient or from a compatible donor. Prior to implantation the contact surface 20 of the biomaterial may be seeded with cells (e.g. chondrocytes, fibroblasts), and the cells may be cultured in vitro to form reconstituted tissues 28 which attaches to and/or physically interlocks with the condensed calcium phosphate material. The resulting biological material comprising the biomaterial and tissues such as cartilage, tendon, ligament attached to the biomaterial may be used to repair/replace localized regions of damaged tissue and to anchor the tissue to bone. In another embodiment, the biomaterial may be seeded with cells and implanted before tissue forms.

Soft and hard connective tissues may be reattached by the anchor 10 having a bone-interfacing portion 16 which has interconnecting pores that extend from the exterior throughout the interior of the condensed calcium phosphate bone-interfacing portion 16 or zone and have a pore size which permits ingrowth of bone; and soft tissue attachment region 18 or interfacing zone which has pores of a pore size which permit ingrowth of soft connective tissue, preferably cartilage, ligament and tendon. More preferably, the soft tissue attachment region 18 of the anchor 10 is seeded with the appropriate cells (e.g. chondrocytes, tendon fibroblasts, ligament fibroblasts, fibroblasts) in vitro and the reconstituted soft connective tissues such as cartilage, tendon, and ligament is attached to and interlocked with the biomaterial.

Figure 3:
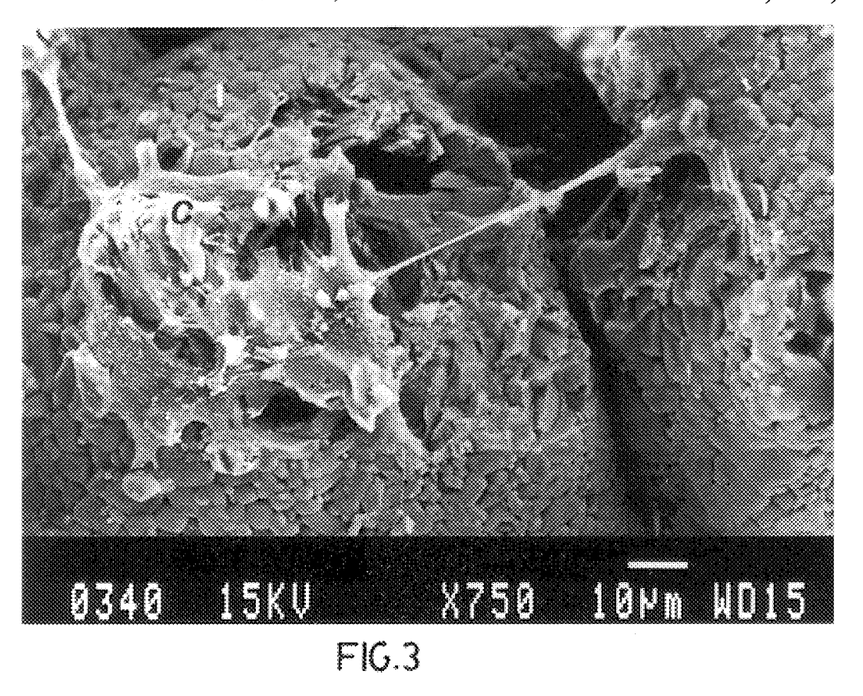
FIG. 3 shows a scanning electron photomicrograph of ligament cells attached to a condensed calcium phosphate.

To avoid cells from soft tissues from interfering with the ingrowth of bone onto the bone interfacing portion 16, the bone interfacing portion 16 is preferably isolated from the soft tissue attachment region 18 during the attachment of soft connective tissues thereon. Soft connective tissue cells are attached to the anchor 10 by positioning the anchor 10 in an inert sterile plastic collar (Bev-A-Line™, Warehouse Plastics Inc., Toronto) and the contact surface 20 of the attachment region 18 is typically seeded with 2.0 to 5.25× $10^6$ chondrocytes with a loading volume of approximately 100 $\mu$l. Preferably, 3.5×$10^6$ cells are seeded per 4 mm disc. Biomaterials can be made and seeded with chondrocytes resulting in the in vitro formation of relatively thick layer of cartilage (e.g. having a thickness of at least 50 $\mu$m). FIG. 3 shows a scanning electron photomicrograph of a ligament cell (indicated "C") attached to bound condensed calcium phosphate crystals of an implant ("I") attachment region. The ligament cell ("C") directly attaches to the crystalline material through cell processes and/or ingress into micropores in the attachment surface of the region of the implant ("I").

Figure 4:
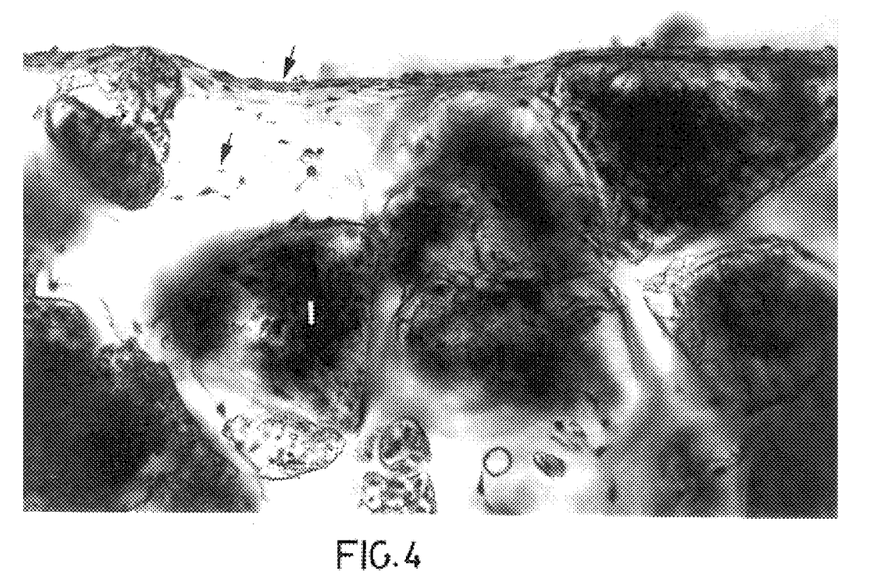
FIG. 4 shows ligament tissues attached and interlocking with pores of a condensed calcium phosphate biomaterial in accordance with the invention.

FIG. 4 shows ligament cells (ie: arrow) attached to a bound condensed calcium phosphate soft tissue attachment region of an implant ("I"). The attachment region is prepared as hereinbefore described. In FIG. 4, the ligament cells attach to crystalline condensed calcium phosphate implant ("I") and there is interlocking of the soft tissue within pores which extend into an in vitro contact surface or face of the implant biomaterial. The formation of connective tissues within the pore of the bound calcium polyphosphate/calcium metaphosphate material thereby physically interlocks the soft connective tissues to the condensed calcium phosphate material ("I").

In another preferred embodiment fibroblasts isolated from ligaments are grown on the biomaterial to form ligamentous tissue. Ligament fibroblasts may be obtained by exposing the joints of an animal, (e.g. bovine), and removing the joints aseptically. The adherent soft tissue is removed, and the ligament harvested and digested using sequential enzyme digestion as described in U.S. Pat. No. 5,326,357 to Kandel. For example, the tissue may be digested with 0.25% pronase, washed, and then digested with 0.1% collagenase. The cells are collected and plated in tissue culture dishes (a density of between about 1×$10^2$ and 1×$10^7$, and preferably 1.3×$10^4$ cells/cm$^2$). After at least one passage, the cells are harvested and resuspended in medium at a concentration of between about 1×$10^2$ to 1×$10^4$ and preferably 5×$10^4$ cells/ml, and 200 $\mu$l are placed on the biomaterial, and grown in suitable culture conditions. Examples of suitable culture medium include Dulbecco's Modified Eagle Medium™ (DMEM). The culture medium preferably contains fetal bovine serum in a concentration range of 0.1–20% and may contain growth factors and ascorbic acid (after day two). The cells are cultured at 37° C. in a humidified atmosphere supplemented with $CO_2$.

An implant made of bound $\beta$-calcium metaphosphate and/or calcium polyphosphate powder with a bone-interfacing portion 16 and a soft tissue attachment region 18 having soft connective tissues 28 attached thereto, may be implanted at the bone/soft tissue interfacing zone into a surgically-prepared site within bone 14 of a patient as is shown in FIG. 2. To implant the anchor 10, the cavity 12 is first formed in the bone 14 by a drill or the like. The cavity 12 is formed of a size and at a location so as to snugly receive the bone interfacing portion 16 of the anchor 10 therein. Most preferably the cavity 12 is formed so that when the bone interfacing portion 16 is inserted therein, the contact surface 20 of the soft tissue attachment portion 18 locates substantially flush with adjacent hard connective tissues of the bone 14, at a site of natural hard connective tissue/soft connective tissue attachment. With time, bone 14 will grow into the bone-interfacing portion 16 of the implant 10 anchoring the biomaterial in position. Simultaneously, the soft connective tissues 28 will grow from the soft tissue attachment portion 18 to join with soft connective tissues in the patient, thereby forming an attachment between the natural (damaged) soft connective tissues and the implant 10. Over time, the soft tissue attachment portion 18 will also degrade, permitting soft connective tissue 28 ingrowth therein to join directly with ingrowing hard connective tissues. The biomaterial degrades at a rate suitable for the rate of in vivo new bone or soft tissue formation. Therefore, eventually the synthetic condensed calcium phosphate biomaterial will substantially degrade and be absorbed leaving in its place a bone-soft tissue complex that is well-bonded recreating the natural soft tissue/hard tissue junction which is suitable for load bearing. The biomaterial may be partly or wholly replaced with tissues of the desired type.

Although the previous embodiments disclose a porous monolithic or composite resorbable biomaterial, the invention is not so limited. The following non-limiting examples are illustrative of further possible uses for the present invention:

EXAMPLE 1

Ligament and Tendon Attachment to Bone

Ligaments and tendons are highly organized dense connective tissue. Injury to ligaments such as the anterior cruciate ligament (ACL) is accompanied by functional joint instability that results in gait abnormalities and muscle atrophy ultimately leading to degenerative arthritis. Growing ligament cells on porous biodegradable calcium polyphosphate/calcium metaphosphate forms or biodegradable organic polymers bonded to such forms would overcome the problems of conventional ligament re-attachment procedures as the tendon would be generated in continuity with the calcium metaphosphate biodegradable material which could then be transplanted as one unit.

Figure 5:
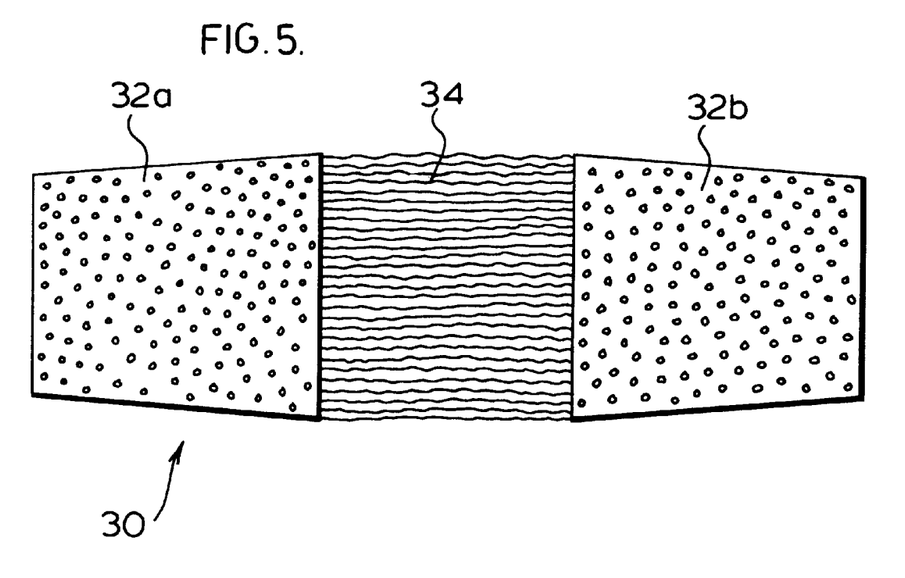
FIG. 5 shows schematically an implantable braid for ligament replacement in accordance with a further embodiment of the invention.

FIG. 5 shows one possible braid construction 30 for use in ligament re-attachment. The braid construction 30 of FIG. 5 includes two bone engaging anchoring members 32$a$,32$b$ which are joined by a fiberous biodegradable organic polymer 34. Each of the anchoring members 32$a$,32$b$ have essentially the same chemical composition as the bone interfacing portion 16 of the anchor device 10 shown in FIG. 1, and comprise crystalline condensed calcium phosphate particles which are bound together into rigid porous implantable structures.

Each end of the fiberous organic polymer 34 is bound to a respective anchoring member 32$a$,32$b$ by melt fusion or other means including crimping, stapling or the like. The organic polymer 34 is selected so as to permit ligament growth thereon either in vivo or more preferably in vitro. Polylactide, polyglycolide (and their copolymers) are two such polymers suitable for use as the polymer 34 in ligament reattachment. In use, ligament cells are seeded along the length of the organic polymer 34 and ligament tissues (not shown) grown in vitro. The tissue/braid 30 construct is then implanted into a patient with each of the anchoring members 32a,32b imbedded into complementary shaped cavities formed in adjacent bones, and with the organic polymer 34 and in vitro formed ligament tissues oriented in a position of natural ligament attachment. The porous condensed calcium phosphate anchor members 32a,32b would then become anchored to bone in vivo through bone ingrowth (assuming that an appropriate porous structure is formed and proper implantation and patient rehabilitation conditions are used). This would in turn allow the effective attachment of the in vitro-formed ligament to bone.

Alternatively, damaged ligament could be re-attached in vivo using a suitably shaped biomaterial seeded with cells.

EXAMPLE 2

Fibrocartilage Repair

Fibrocartilage (ie. temporomandibular joint (TMJ) and intervertebral discs) has a limited ability to repair itself and at present there are few treatment options. Allograft transplants are limited by donor availability and carry with them the risk of disease transmission. The patient's chondrocytes may be seeded on an implant of condensed calcium phosphate (formula $[Ca(PO_3)_2]_n$, where n is greater than 3) which serves as porous support for tissue formation and provides an effective structure with which the newly-formed tissues can interlock. The chondrocytes per se do not enter the interior of the porous scaffold although cells may be entrapped in pores that open to the surface of the condensed calcium phosphate. Porous calcium metaphosphate provides an ideal substrate for this process and, as it is compatible with bone, could be implanted as a tissue engineered composite to allow anchoring, of the in vitro-formed fibrocartilage to host bone.

EXAMPLE 3

Artificial Bone Implant/Gap Filler

For the treatment of fractures involving extensive bone destruction or replacement of resected diseased bone, it is often necessary to bridge large gaps with a scaffolding substance. Current methods to replace bone that has been resected because of disease or malignancy require either taking autologous bone from the iliac crest which is painful and not always feasible or using "inert" artificial nonbiodegradable materials (CoCr alloys, titanium alloys, alumina). Autografting is the most common approach for so doing but requires an additional surgical site with increased risk to the patient. The use of allografts introduces further possible complications through disease transfer and immunological response. Hence, a need exists for an appropriate biodegradable synthetic bone substitute material. The present invention therefore provides a better alternative in the use of a porous structure comprising bound crystalline β-calcium metaphosphate and/or calcium polyphosphate particles which can be remodelled and eventually replaced by the patient's own bone.

A potential use for a substantially non-porous resorbable biomaterial comprising calcium metaphosphate either alone or with a degradable organic phase is for fabricating implants for use in fracture repair procedures. The major advantage of a degradable fracture repair implantable device is that its use would avoid a need for a second procedure to remove a non-degradable implant. In addition, the use of a slowly degrading fixation plate made of condensed calcium phosphate with or without a degradable organic phase that would become less stiff with time as the fractured bone healed would offer an advantage of avoiding undesirable bone loss resulting from stress shielding of the bone by a stiff plate as well as possibly allowing faster fracture healing (if plate stiffness can be tailored to allow stress stimulation of cell differentiation and osteogenesis during the early reparative phase of fracture healing).

EXAMPLE 4

Bone Defect Repair/Periodontal Defect Fillers

The use of unbound calcium polyphosphate and/or calcium metaphosphate powder may be used as particulate matter to fill a defect. This is the case, for example, around a periodontally-compromised natural tooth, wherein a condensed calcium phosphate powder having a mean particle size of less than 100 μm may be used to infill around dentin and/or dental implants. The application of the powder as fill is an attractive possibility particularly if the degradation rate of the powders can be appropriately tailored to match the bone formation rate at the implant junction.

A similar implant-related application exists in the orthopaedic field. The replacement of diseased skeletal joints with prosthetic implants is not unlike the procedure used for dental implant placement. Both involve the placement of a device into a prepared site (usually) with a desired condition (often a necessary one for long term success) being initial stability of the implant in the site. The use of a powder condensed calcium phosphate filler material may be used where a tight implant fit cannot otherwise be achieved or when bone fragility prevent the use of press fit implants.

Trial Example 1

Condensed calcium phosphate powders consisting of calcium polyphosphates and calcium metaphosphates of the general formula $[Ca(PO_3)_2]_n$, with n at least 3, were formed from calcified calcium phosphate monobasic, $Ca(H_2PO_4)_2H_2O$. The resulting $[Ca(PO_3)_2]_n$ powder was melted and poured onto a graphite plate to produce a solid piece of calcium metaphosphate glass displaying an amorphous structure as a result of the rapid cooling process. The hot glass was further quenched by dropping into distilled water resulting in shattering of the glass to produce a powder frit. This frit was further ground to form a −100/+60 mesh condensed calcium phosphate powder of the formula $[Ca(PO_3)_2]_n$, where n was 3 or more and the Ca:P molar ratio was between about 0.4 and 0.6.

Porous rods were prepared by packing the calcium metaphosphate powder into platinum tubes (average packing density=54% of full density often referred to as % theoretical density) and gravity sintering just below the melting temperature to form rods of 57% theoretical density. Despite the relatively small increase in density, the rods displayed acceptable fracture resistance.

Following sintering, approximately 4 mm diameter×6 mm long rods were implanted into rabbit femurs for a preliminary investigation of bone ingrowth characteristics. The rods were cut to length with a diamond wafering blade, cleaned hydrosonically in distilled water and autoclaved. They were implanted in the distal region of the femur of New Zealand white rabbits by drilling holes normal to the axis of the bones and press fitting the rods into these sites such that less than 1 mm protruded above the periosteal surface.

X-ray diffraction was used to confirm the structure of glass powder and sintered rods and the absence of crystalline structure in the glass powder. The powders and sintered rods were analyzed by scanning electron microscopy (SEM) to characterize the shape and size of both the particles used for sinter processing and the final sintered structures. Density measurements of sintered rods were used to estimate porosity based on percentage of theoretical density.

Figure 6:
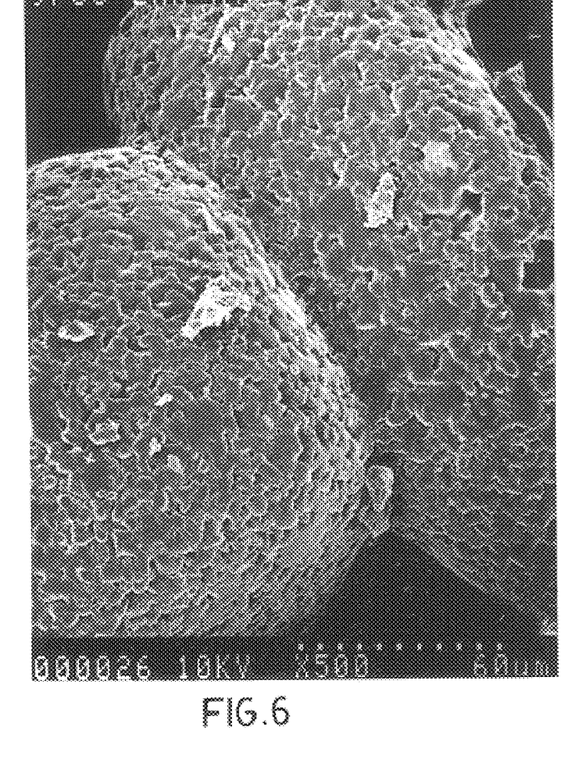
FIG. 6 is a scanning micrograph of a typical neck between sintered particles (150–250 μm size) of a biomaterial for use in the present invention.

FIG. 6 shows a typical neck between particles sintered as described above verifying the extensive neck formation due to diffusion that resulted in strong sintered samples despite the relatively small increase in density noted upon sintering (54% to 57% theoretical density).

The rods were implanted into rabbits for periods of 2 days, 2, 6 and 12 weeks. Preliminary observations from the rabbit implantation studies indicated that the sinewed condensed calcium phosphate rods were well tolerated by the surrounding tissue.

Figure 7:
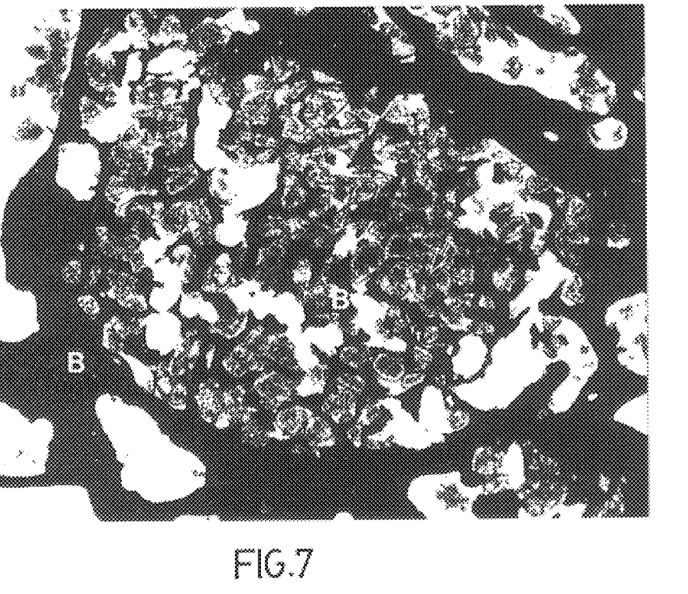
FIG. 7 is a photomicrograph of a histological section of a rabbit femur showing a biomaterial of the invention with ingrowth of bone into the pores of the biomaterial.

FIG. 7 shows a photomicrograph of a histological section of femur. A crystalline condensed calcium phosphate implant (shown by "arrow") comprising calcium metaphosphate and/or calcium polyphosphate in accordance with the invention was placed in the femur and harvested after 12 weeks. There is ingrowth of bone (indicated "B") throughout the implant. Surprisingly, FIG. 7 shows no cellular nor fibrotic reaction with the resorbable biomaterial of the invention. Pre-existing bone (B) is seen around the implant (4 mm diameter) (von Kossa stain with toluidine blue counterstain).

In vivo implantation studies with the condensed calcium phosphate implant in the hard connective tissue (e.g. bone) indicate that it is well tolerated by the surrounding tissues and it does not invoke an unfavourable cellular reaction or fibrotic response. The use of crystalline condensed calcium phosphate with interconnected pores in the biomaterial provides a non-toxic biomaterial which degrades. Further, the crystalline form of the condensed calcium phosphate has been found to degrade at a suitable rate having regard to the rate of tissue growth therein. The biomaterial after implantation is eventually substantially degraded and absorbed leaving in its place a new natural soft connective tissue-bone junction that is well-bonded and functional.

Trial Example 2

Culturing of Cells onto Condensed Calcium Phosphate Discs

Chondrocytes were obtained from bovine metacarpal-carpal joints using methods described by U.S. Pat. No. 5,326,357 to Kandel or using a method described previously (Kandel et al In Vitro Cell Dev. Biol 33:174–181, 1997). In an experiment, cells from full thickness cartilage were then placed on porous condensed calcium phosphate discs (4 mm diameter×2 mm thick) and maintained in Hams F12 with fetal bovine serum. On day 7, ascorbic acid (final concentration 100 μg/ml) was added to the medium. The cells were grown at 37° C. in a humidified atmosphere supplemented with 5% $CO_2$. Medium was changed every two days and fresh ascorbic acid was added with each change of medium.

To examine whether the chondrocyte cultures are accumulating matrix, the cultures were harvested at 30 days. They were fixed in 10% formalin, embedded in acrylic because of the hard calcium metaphosphate substrate and sections cut and stained with either haematoxylin and eosin, or toluidine blue. The toluidine blue stained sulphated proteoglycans in the extracellular matrix. A continuous layer of cartilaginous tissue formed on the top of the biomaterial and within the pores opening to the top.

Figure 8:
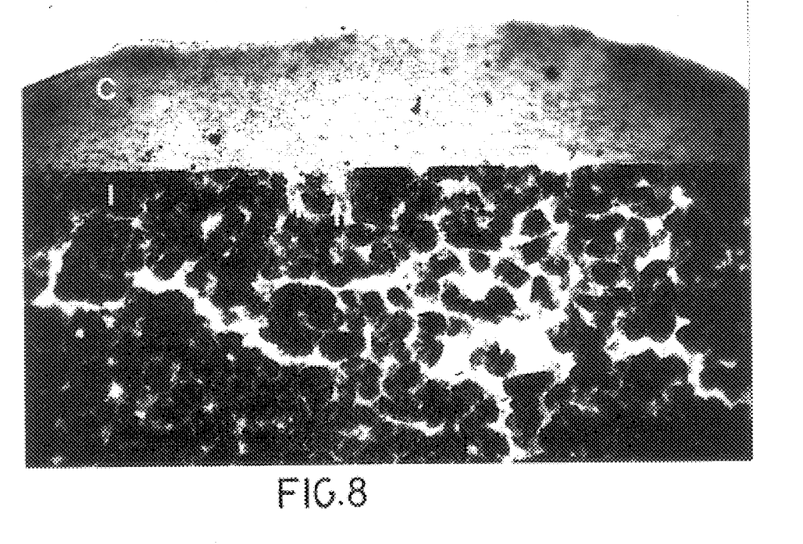
FIG. 8 is a photomicrograph of a histological section of a condensed calcium phosphate biomaterial/cartilage tissue construct showing the interlock of cartilage tissue with the pores of the soft tissue attachment surface.

FIG. 8 is a photomicrograph of a histological section of condensed calcium phosphate material ("I"), and cartilage tissue ("C"). Chondrocytes were isolated from articular cartilage, placed on the condensed calcium phosphate material and grown in culture for 30 days. The chondrocytes accumulated extracellular matrix and formed cartilage on the material.

FIG. 8 shows the attachment of cartilage tissues ("C") to a soft tissue attachment portion of a condensed calcium phosphate biomaterial. The attachment portion of the implant ("I") is characterized by non-linear interconnecting pores which extend into a contact surface contiguous with the soft tissue. The extension of the pores into the contact surface presents open cavities in which cartilage tissue ("C") forms to physically interlock the soft tissue ("C") with the attachment portion ("I") as is shown by the arrows.

Fibroblasts isolated from ligaments may be grown on porous condensed calcium phosphate discs to form ligamentous tissue. Ligament tissue is harvested from bovine knee joints aseptically. The cells are isolated by pronase-collagenase digestion (Kandel et al In Vitro Cell Dev. Biol. 33:174–181, 1997). The cultures may be harvested at varying times and the formation of ligamentous tissue will be determined histologically as described above. The sections are then stained with trichrome to determine whether collagen is present.

Trial Example 3

Processes for Preparing Biomaterials

A solution of analytical grade of calcium carbonate ($CaCO_3$) in orthophosphoric acid ($H_3PO_4$) (88 M %) is prepared by slow mixing with constant stirring. After drying at 200° C. for 12 hours, the dried batch is melted in a Pt crucible by heating to 1100° C. and holding for one hour in air. The melt is solidified by quenching from the melt to form an amorphous condensed calcium phosphate glass that is subsequently annealed at 600° C. for 10 minutes and furnace cooled to room temperature.

To form the porous substrate one of two methods is used. In one process the glass is recrystallized by heating to 850° C. at 200° C./h (approx.) and held for 24 to 48 hours followed by furnace cooling to room temperature. The resulting glass-ceramic is leached with 0.1 N HCl at 37° C. to obtain a porous bound material.

In another process, the bulk glass sample is ground to <50 micron-sized particles. To obtain a porous ceramic, the ground particles are mixed with a foaming agent ($CaCO_3$) and pressed to form a preform. The mixture is heated to above the glass transition temperature ($T_g$). Sintering of the glass particles occurs at this temperature with simultaneous entrapment of the $CaCO_3$ particles that then react to give off $CO_2$ gas. This gaseous exudate results in pore formation within the low viscosity glass.

Pore size, shape (pores or channels) distribution, directionality (of the channels), and volume percent porosity can be varied by controlling melt temperature, cooling rate, and direction of heat removal in the first process, and sintering time and temperature as well as amount of $CaCO_3$ present in the second method. Pore sizes up to 300 microns in diameter have been formed using the processes described above.

Although FIGS. 1 and 2 illustrate a frustoconical shaped anchor 10, the invention is not so limited. The anchor 10 could equally be formed having almost any other shape, including those of conventional mechanical screws, pins, braids and the like.

Although the preferred embodiments of the invention describe the use of the present invention for attaching soft to hard connective tissues, the invention is not so limited. In its porous form, the calcium metaphosphate and/or calcium polyphosphate with or without an organic filler phase could be used as a bone substitute or bone augmentation material alone (both dental and orthopaedic applications are envisaged).

Figure 9:
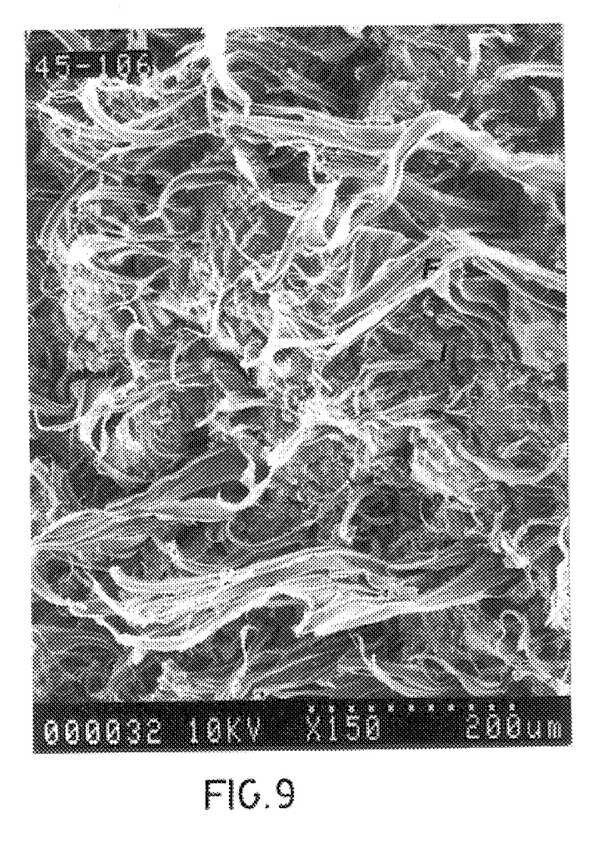
FIG. 9 is a scanning electron micrograph showing polycaprolactone infiltrated condensed calcium phosphate.

In any of the aforementioned applications, the organic phase may be used to strengthen or toughen the implant. FIG. 9 shows a polycaprolactone (indicated "F") infiltrated bound crystallized condensed calcium phosphate structure or implant (indicated "I"). The condensed calcium phosphate/polycaprolactone composite structure ("I") is shown after mechanical testing which resulted in fracture. The fibrilar appearing elements consist of polycaprolactone polymer ("F") which has been partially physically extended from the pores within the condensed calcium phosphate ("I") as a result of tensile forces. The extension of the polycaprolactone polymer ("F") illustrates energy absorption during fracture (ie. toughening) and substantially complete infiltration into the pores of the condensed calcium phosphate structure ("I").

As a dense material, the condensed calcium phosphate, calcium metaphosphate, calcium polyphosphate or mixtures thereof could be used to form novel biodegradable/absorbable bone screws, plates and pins for use in bone fracture repair (e.g. re-attachment of bone chips, repair of fractures across the growth plate in children and adolescents, or fixation of biodegradable fracture fixation plates during osteosynthesis in all age groups).

The crystal (grain) structure of the crystallized condensed calcium phosphate can be varied by choosing different rates of heat-up during the crystallization anneal and by selecting different hold times at the annealing temperatures. More rapid heating rates will result in higher crystal nucleation rates and hence, finer crystal size. This will result in a different degradation rate, with finer crystal size giving faster degradation rates. Sintering temperature used during preparation of porous forms may also be influenced by grain size. By example, the structure shown in FIG. 6 have a crystal size of aproximately 5 to 10 micron and were formed using a 10° C./min. heat-up rate. It is to be appreciated that the size of the crystals is selected having regard to the desired degradation rate of the implant for its intended placement.

Having illustrated and described the principles of the invention in a preferred embodiment, it should be appreciated to those skilled in the art that the invention can be modified in arrangement and detail without departure from such principles. Although the disclosure describes and illustrates preferred embodiments of the invention, it is to be understood that the invention is not so limited. Many variations and modifications will now occur to those skilled in the art. For a definition of the invention, reference may be had to the appended claims.

We claim:

1. An implant for use in connecting soft and hard connective tissues comprising, a hard tissue interfacing portion, and a soft tissue attachment portion, said hard tissue interfacing portion comprising condensed calcium phosphate particles which are joined together to form a rigid matrix characterized by interconnecting spaces between said condensed calcium phosphate particles that extend from an exterior substantially throughout an interior of at least part of said hard tissue interfacing portion, said condensed calcium phosphate particles represented by the general formula (1):

$$[Ca(PO_3)_2]_n \quad (1)$$

where n is at least 3, and the molar ratio of Ca to P is between about 0.4 to 0.6, said interconnecting spaces having a pore size which permits bone cells and tissues to penetrate and grow therein.

2. An implant as claimed in claim 1 wherein said pore size of said interconnecting spaces is between about 50 to 250 μm.

3. An implant as claimed in claim 1 wherein said condensed calcium phosphate includes crystalline calcium metaphosphate, and said hard tissue interfacing portion further includes a biodegradable organic strengthener substantially interspersed within at least part of said interconnecting spaces, said strengthener selected from the group consisting of polycaprolactone, polyglycolide, polylactide and their copolymers.

4. An implant as claimed in claim 3 wherein said condensed calcium phosphate particles comprise crystalline β-calcium metaphosphate particles of the general formula (1), and wherein n is 100 or greater.

5. An implant as claimed in claim 1 wherein said soft tissue attachment portion comprises bound condensed calcium phosphate particles represented by formula (1), said soft tissue attachment portion having interconnecting pores having a size of less than about 200 μm.

6. An implant as claimed in claim 5 wherein said soft tissue attachment portion comprises a biodegradable organic polymer selected from the group consisting of polycaprolactone, polylactide, polyglycolide and their copolymers.

7. An implant as claimed in claim 5 further comprising soft connective tissue cells joined to said soft issue attachment portion at least in part by ingrowth into said pores.

8. An implant as claimed in claim 7 wherein said soft tissue attachment portion includes a soft tissue contact surface juxtapositioned with said soft tissue cells, at least some of said interconnecting pores extending into said contact surface and presenting cavities permitting interlocking of soft connective tissues and said soft tissue attachment portion.

9. A method of preparing an implant for attaching soft and hard connective tissues characterized by a hard tissue interfacing portion and a soft tissue attachment portion, each of said hard tissue interfacing portion and said soft tissue attachment portion comprising joined condensed calcium phosphate particles represented by the general formula (1):

$$[Ca(PO_3)_2]_n \quad (1)$$

where n is at least 3 and the Ca:P molar ratio is between about 0.4 and 0.6, the method including the steps of:

forming said condensed calcium phosphate powder into a desired implant shape having said hard tissue interfacing portion and said soft tissue interfacing portion, sintering the condensed calcium phosphate particles to form said implant shape into rigid structure, and seeding at least part of the soft tissue attachment portion with cell material in vitro, said cell material obtained from soft connective tissues selected from the group consisting of tendons, ligaments, intervertebral disc, and cartilage.

10. A method as claimed in claim 9 wherein said cell material comprises cells obtained from a host site for the implant.

11. A method as claimed in claim 9 wherein prior to said step of forming said implant shape said powder is formed by the steps of:

calcining calcium phosphate monobasic to form condensed calcium phosphate having the molecular structure represented by the formula (1):

$$[Ca(PO_3)_2]_n \qquad (1)$$

where n is 100 or greater and the molar ratio of Ca/P is selected at about 0.5; and sizing said condensed calcium phosphate powder used to form said hard tissue interfacing portion to a mean particle size selected between about 5 and 250 μm.

12. A method as claimed in claim 9 wherein said cell material comprises cells and said method includes the further step of culturing the cells in vitro prior to implantation of the implant.

13. A method as claimed in claim 12 wherein at least part of said hard tissue interfacing portion is characterized by interconnecting spaces and prior to said step of seeding, substantially infilling at least some of said interconnecting spaces with a biodegradable organic strengthener selected from the group consisting of polycaprolactone, polyglycolide, polylactide and their copolymers.

14. A method as claimed in claim 9 wherein at least part of said hard tissue interfacing portion is characterized by interconnecting spaces and said method includes the further steps of infilling at least some of said interconnecting spaces with a biodegradable organic strengthener, and contacting a peripheral portion of said part of said hard tissue interfacing portion with a solvent to selectively remove said organic strengthener from said peripheral portion.

15. A method as claimed in claim 14 wherein said organic strengthener is selected from the group consisting of polycaprolactone, polyglycolide, polylactide, and their copolymers.

16. A method of treating deficient hard tissue and soft tissue attachment in a patient by the use of an implant comprising a hard tissue interfacing portion and a soft tissue attachment portion, said hard tissue interfacing portion including crystalline condensed calcium phosphate particles of the formula (1):

$$[Ca(PO_3)_2]_n \qquad (1)$$

where n is at least 3 and the molar ratio of Ca:P is between about 0.4 and 0.6, said particles joined to form a matrix characterized by interconnecting spaces which extend from an exterior throughout an interior of said matrix, the interconnecting spaces having a pore size which permits hard connective tissue cells and tissues to penetrate therein, said method comprising the steps of:

preparing a recipient site in said patient's hard tissue, said recipient site having a complementary size and shape to said hard tissue interfacing portion of said implant, and inserting said implant in said recipient site with said hard tissue interfacing portion substantially in juxtaposition said patient's hard tissues and said soft tissue attachment portion positioned substantially at a site of natural hard tissue/soft tissue attachment.

17. A method as claimed in claim 16 comprising the further step of seeding said soft tissue attachment portion with soft connective tissue cell material in vitro prior to said implanting step.

18. A method as claimed in claim 17 wherein said soft tissue cell material comprises cells isolated from said patient.

19. An implant for connecting bone tissue and soft connective tissues in a human comprising, a bone tissue interfacing portion, a soft tissue attachment portion, and soft connective tissue cells attached to said soft tissue attachment portion, said cells obtained from soft tissues selected from the group consisting of tendons, ligaments, cartilage and intervertebral disc, said bone tissue interfacing portion comprising a biodegradable particulate material which is bound to form a rigid matrix characterized by interconnecting pores which extend from an exterior substantially through an interior of said bone tissue interfacing portion, the pore size of said interconnecting pores selected at between about 50 to 250 μm, and said soft tissue attachment portion being characterized by pores having a pore size selected at less than 200 μm, and wherein said pores of said soft tissue attachment portion are provided in substantially non-linear communication.

20. An implant as claimed in claim 19 wherein said particulate material includes β-calcium metaphosphate powder.

21. An implant as claimed in claim 19 wherein said soft tissue attachment portion comprises, a contact surface juxtaposed with said soft connective tissue cells, and non-linear interconnecting pores having an average cross-sectional dimension selected at less than about 200 microns, at least some of said interconnecting pores extending into said contact surface and presenting cavities permitting physical interlocking of soft connective tissues and said soft tissue attachment portion.

22. An implant as claimed in claim 19 wherein said particulate matter comprises crystalline condensed calcium polyphosphate powder which is characterized by condensed calcium polyphosphate crystals having a mean crystal size selected in relation to the desired degradation rate of said implant.

23. A resorbable biomaterial for implantation into an animal including a crystalline condensed calcium phosphate powder comprising calcium metaphosphate, said condensed calcium phosphate represented by formula (1):

$$[Ca(PO_3)_2]_n \qquad (1)$$

wherein n is at least 3, and the molar ratio of Ca:P is between about 0.4 to 0.6, and wherein said calcium metaphosphate comprises particulate calcium metaphosphate bound into a rigid implantable structure which includes a soft tissue attachment structure characterized by a soft tissue contact surface, wherein at least part of said implantable structure is characterized by interconnecting pores extending from an exterior of the biomaterial throughout an interior of said part, and wherein the pores have an average cross-sectional dimension selected at between about 1 to 1000 microns, said resorbable biomaterial further comprising in vitro cultured soft connective tissue attached to said implantable structure, and at least some of said pores extending into said contact surface and presenting cavities permitting the physical interlocking of said soft connective tissue and said implantable structure.

24. A resorbable biomaterial as claimed in claim 23 further comprising a bioactive agent at least partially interspersed in said pores, said bioactive agent selected from the group consisting of proteins, peptides, nucleic acids, polysaccharides, lipids, non-protein organic compounds and inorganic compounds.

25. A resorbable biomaterial as claimed in claim 23 further comprising a biodegradable organic strengthener substantially infilling said interconnecting pores, said organic strengthener selected so as to degrade at a faster degradation rate than said condensed calcium phosphate following implantation into said animal.

26. A resorbable biomaterial as claimed in claim 25 wherein said condensed calcium phosphate comprises β-calcium metaphosphate.

27. A resorbable biomaterial as claimed in claim 25 wherein said organic strengthener is selected from the group consisting of polycaprolactone, polyglycolide, polylactide and their copolymers.

* * * * *